United States Patent [19]

Imaki et al.

[11] Patent Number: 4,640,931

[45] Date of Patent: Feb. 3, 1987

[54] 3-(INDIAN-5-YLOXY (OR THIO)) CYCLOPENTANECARBOXYLIC ACID ANALOGUES

[75] Inventors: Katsuhiro Imaki, Kyoto; Tadao Okegawa, Yawata; Yoshinobu Arai, Osaka, all of Japan

[73] Assignee: Ono Pharmaceutical Co., Ltd., Osaka, Japan

[21] Appl. No.: 792,399

[22] Filed: Oct. 29, 1985

[30] Foreign Application Priority Data

Oct. 29, 1984 [JP] Japan ................................. 59-225818

[51] Int. Cl.$^4$ ................... C07C 149/40; A61K 31/215
[52] U.S. Cl. ..................................... 514/510; 514/569; 560/10; 560/53; 562/428; 562/462
[58] Field of Search ................... 560/10, 53; 562/428, 562/462; 514/510, 569

[56] References Cited

U.S. PATENT DOCUMENTS 3,776,944 12/1973 Brown .................................. 560/53
3,984,465 10/1976 Cragoe ................................. 560/53

FOREIGN PATENT DOCUMENTS 47011 3/1982 European Pat. Off. .............. 560/53

OTHER PUBLICATIONS

Wagner, "Synthetic Organic Chemistry," pp. 226–229 & 787–788 (1953).

*Primary Examiner*—Michael L. Shippen
*Attorney, Agent, or Firm*—Sughrue, Mion, Zinn, Macpeak, and Seas

[57] ABSTRACT

The present invention relates to novel compounds of the general formula:

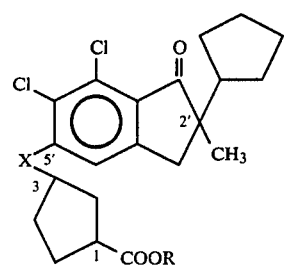

(I)

wherein X represent an oxygen atom or a sulfur atom and R represents a hydrogen atom or an alkyl group of 1–4 carbon atoms, and non-toxic salts thereof when R represents a hydrogen atom, possessing an inhibitory effect on cerebral edema.

7 Claims, No Drawings

3-(INDIAN-5-YLOXY (OR THIO)) CYCLOPENTANECARBOXYLIC ACID ANALOGUES

INDUSTRIAL UTILITY

This invention relates to new 3-(indan-5-yloxy (or thio)) cyclopentanecarboxylic acid analogues. In detail description, it relates to 3-[(2-cyclopentyl-2-methyl-6,7-dichloro-1-oxoindan-5-yl)oxy (or thio)]cyclopentanecarboxylic acid compounds, their alkyl esters, processes for their preparation and treating agents for cerebral edema containing them as active ingredient.

PRIOR ARTS

Heretofore, 5-substituted-indan-1-one analogues for the purpose of treatment of cerebral edema have been known. For example, it was proposed that in the specification of the European Patent Publication No. 47011, the compounds represented by the general formula:

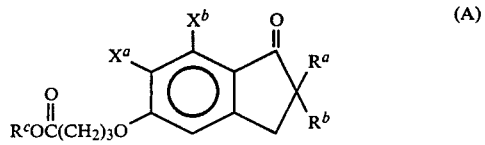

(wherein $X^a$ and $X^b$ represent a halogen atom, $R^a$ represents a lower alkyl group of 1-6 carbon atoms, $R^b$ represents a hydrogen atom, a lower alkyl group of 1-4 carbon atoms, a cycloalkyl group of 3-6 carbon atoms, a lower cycloalkyl-lower alkyl group of 4-7 carbon atoms, or a phenyl and $R^c$ represents a hydrogen atom, a lower alkyl group of 1-6 carbon atoms or a carboxy-lower alkyl group of 2-6 carbon atoms.) and their salts, may be used for treatment of cerebral edema.

In the general formula (A), the compound wherein $X^a$ and $X^b$ represent chlorine atoms, $R^a$ represents a methyl group and $R^c$ represents a hydrogen atom, i.e. (+)-4-[((2R)-2-cyclopentyl-2-methyl-6,7-dichloro-1-oxoindan-5-yl)oxy]butyric acid of the formula:

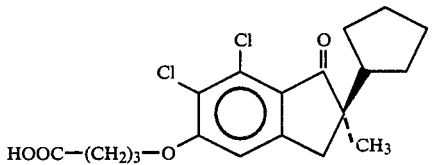

has been known as "DCPIB", and whose inhibitory effect on cerebral edema was described in Journal of Medicinal Chemistry, Vol. 25 (No. 5), 567 (1982).

PROBLEM TO BE SOLVED

The inhibitory effect of DCPIB on cerebral edema is strong, but the effect is not enough to use in practice.

MEANS TO SOLVE THE PROBLEM

For the purpose of finding the compound whose inhibitory effect on cerebral edema is stronger than DCPIB, we noted a trimethylene group (—(CH₂)₃—) between an indanyloxy group and a carboxy group in a side chain of DCPIB and we synthesized various compounds which have a cycloalkylene group

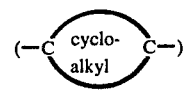

or a cycloalkylene-alkylene group

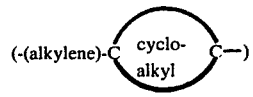

instead of the group, and examined their pharmacological activity. As a result of the examination, generally in the case of the compounds substituted by a cyclopropylene or cyclohexylene group, their inhibitory effect on cerebral edema was equal to or weeker than DCPIB and in the case of the compounds substituted by cyclopentylene group, the effect of the compounds substituted by a 1,2-cyclopentylene or cyclopentylenealkylene group was not better. Unexpectedly, it has now been found that the effect of the only compounds substituted by 1,3-cyclopentylene group was much better, having completed this invention.

CONSTITUTION OF THE INVENTION

According, the present invention relates to 3-(indan-5-yloxy (or thio)) cyclopentanecarboxylic acid analogues of the general formula:

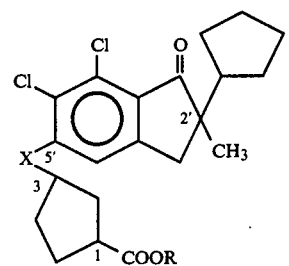

(wherein X represents an oxygen atom or a sulfur atom and R represents a hydrogen atom or an alkyl group of 1-4 carbon atoms.), their non-toxic salts when R represents a hydrogen atom, processes for their preparation and treating agents for carebral edema containing them as active ingredient.

In the general formula (I), the alkyl groups represented by R are a methyl, ethyl, propyl and butyl groups, and isomers thereof and all of them are preferable. And the compounds whose R represents a hydrogen atom are preferable, too.

In the compounds of the general formula (I), there are apparently at least three asymmetiric carbon atoms. Those are the carbon atom at the 2-position of an indan skeleton and the carbon atoms at the 1- and 3-positions of a cyclopentylene group in the side chain substituted to the carbon atom at the 5-position of an indan skeleton. Further, when R represents a branched-chain alkyl group, other asymmetric centers may occur. It is well known that the isomer arises in the cause of existence of an asymmetric center. However, the compounds of the general formula (I) comprises all the isomers and mixture thereof.

As for the stereo-configuration of the carbon atom at the 2-position of an indan skeleton, R-configuration, S-configuration and the mixture thereof (i.e. RS) are preferable, and S- or RS-configuration is more preferable. As for the stereo-configuration of the carbon atoms at the 1- and 3-positions of a cyclopentylene group, (1S, 3S), (1R, 3R), (1S, 3R) and (1R, 3S) are preferable, and (1S, 3S) and (1R, 3R) which are composed a trans-configuration each other, are more preferable and above all (1S, 3S) is the most preferable.

Preferred compounds of the general formula (I) of the present invention are, for example, as follows:

1,3-trans-3-[((2RS)-2-cyclopentyl-2-methyl-6,7-dichloro-1-oxoindan-5-yl)oxy]cyclopentanecarboxylic acid, 1,3-trans-3-[((2RS)-2-cyclopentyl-2-methyl-6,7-dichloro-1-oxoindan-5-yl)thio]cyclopentanecarboxylic acid, 1,3-trans-3-[((2S)-2-cyclopentyl-2-methyl-6,7-dichloro-1-oxoindan-5-yl)oxy]cyclopentanecarboxylic acid, 1,3-trans-3-[((2S)-2-cyclopentyl-2-methyl-6,7-dichloro-1-oxoindan-5-yl)thio]cyclopentanecarboxylic acid, (1S, 3S)-3-[((2RS)-2-cyclopentyl-2-methyl-6,7-dichloro-1-oxoindan-5-yl)oxy]cyclopentanecarboxylic acid, (1S, 3S)-3-[((2RS)-2-cyclopentyl-2-methyl-6,7-dichloro-1-oxoindan-5-yl)thio]cyclopentanecarboxylic acid, (1S, 3S)-3-[((2S)-2-cyclopentyl-2-methyl-6,7-dichloro-1-oxoindan-5-yl)oxy]cyclopentanecarboxylic acid, (1S, 3S)-3-[((2S)-2-cyclopentyl-2-methyl-6,7-dichloro-1-oxoindan-5-yl)thio]cyclopentanecarboxylic acid, and their methyl esters, and their non-toxic salts.

PROCESS

According to the present invention, the compounds of the present invention represented by the general formula (I) can be produced by the processes hereinafter mentioned.

(Method A)

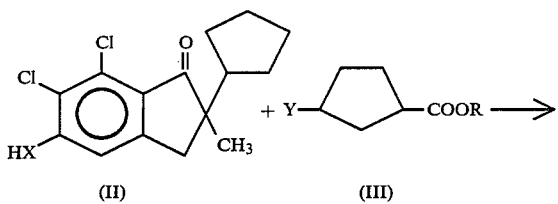

(II)                (III)

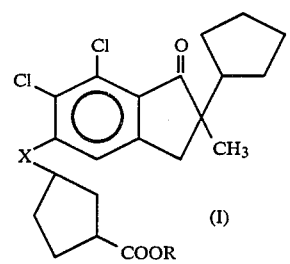

(I)

(Method B)

-continued

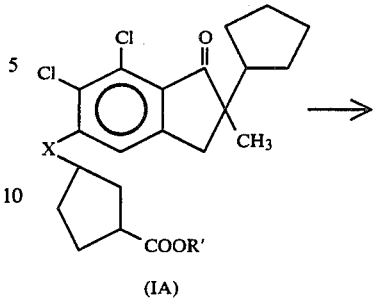

(IA)

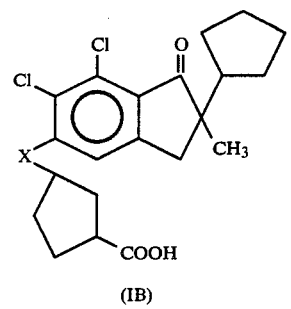

(IB)

wherein Y represents a halogen atom (e.g. a chlorine, bromine or iodine atom), or an unsubstituted- or substituted-alkylsulfonyloxy or arylsulfonyloxy group (e.g. a methanesulfonyloxy or p-toluenesulfonyloxy group), R' represents an alkyl group of 1–4 carbon atoms, and X is as hereinbefore defined.

(Method A) may be carried out by reacting the compounds of the general formula (II) and those of the general formula (III), in the presence of a base, e.g. such a hydride of alkali metal as sodium hydride, such an alkoxide of alkali metal as sodium ethoxide or such a carbonate or hydroxide of alkali metal as potassium carbonate or sodium hydroxide, in such an inert organic solvent as tetrahydrofuran, dimethylformamide, dimethylsulfoxide, hexamethylphosphoramide or dimethoxyethane or the mixture thereof, at a temperature from 0° C. to a reflux temperature of the reaction mixture, preferably at a temperature from room temperature to 60° C.

(Method B) is a saponification reaction and may be carried out by the reaction in the presence of a solvent soluble in water, for example tetrahydrofuran or an alkanol of 1–4 carbon atoms (e.g. methanol), using an aqueous solution of a hydroxide or carbonate of an alkali metal, for example, lithium, sodium or potassium, at a temperature from 0° C. to a room temperature.

The compound of the general formula (II) used as a starting material may be prepared by the method described in the specification of the U.S. Pat. Nos. 3,984,465, 4,081,554 and 4,085,219, and the European Patent Publication No. 47011. The compound of the general formula (II) wherein X represents a sulfur atom may be prepared from the compound of the general formula (II) wherein X represents an oxygen atom according to the following Scheme.

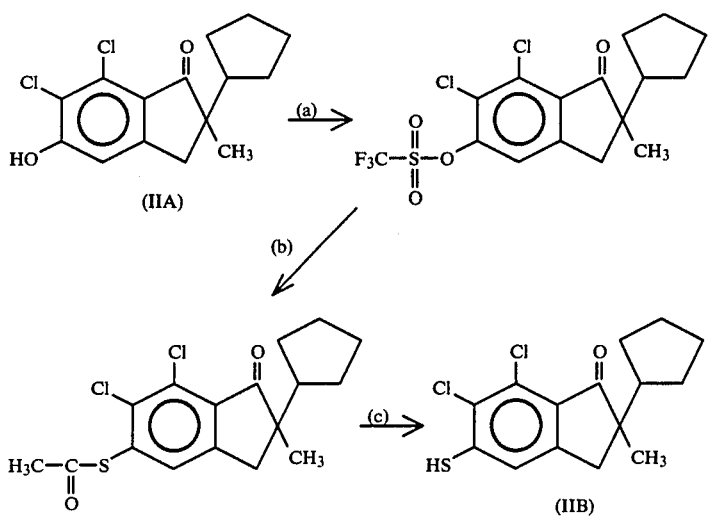

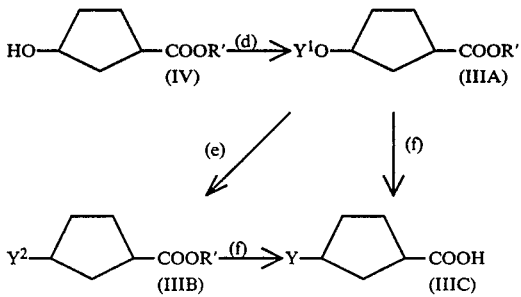

The step (a) may be carried out by using trifluoromethanesulfonyl chloride under the above-mentioned condition for (Method A), the step (b) may be carried out by using thioacetic acid or its sodium salt, in the presence of diisopropylethylamine, in dimethylformamide at ambient, and the step (c) may be carried out by the same method as above-mentioned for (Method B). The optical active compounds of the general formula (II) may be prepared by the method described in the above-mentioned patent specifications.

The compound of the general formula (III) used for another starting material may be prepared according to the following Scheme.

Wherein $Y^1$ represents an unsubstituted or substituted alkylsulfonyloxy or arylsulfonyloxy group, $Y^2$ represents a halogen atom and the other symbols are as hereinbefore defined.

The step (d) may be carried out by reacting with such an alkylsulfonyl chloride as mesyl chloride or such an arylsulfonyl chloride as tosyl chloride (a) in the presence of such a tertiary amine as pyridine or triethylamine, in such an inert organic solvent as methylene chloride or (b) in pyridine, at a temperature from $-30°$ C. to $50°$ C.

The step (e) may be carried out by using a halide of alkali metal, for example, such a lithium halide as lithium chloride, lithium iodide or lithium bromide, or sodium iodide, in an inert organic solvent, for example, acetone, dimethylformamide, dimethylsulfoxide or hexamethylphosphoramide, at a temperature from a room temperature to $60°$ C.

The step (f) may be carried out by the same method as above-mentioned for (Method B).

The compound of the general formula (IV) may be easily prepared from 3-oxocyclopentanecarboxylic acid by known methods. For example, 3-oxocyclopentanecarboxylic acid may be converted into the corresponding alkyl ester by using a diazoalkane, and then reducing an oxo group at the 3-position of the obtained ester into a hydroxy group by using a known reducing agent (e.g. sodium borohydride) to give the compounds of the general formula (IV). The reduction must be carefully carried out to avoid any reduction of the carboxyl moiety. The optical active compound of general formula (III) may be prepared by the same procedure from an optical active 3-oxocyclopentanecarboxylic acid as a starting material and further, if desired, separated and purified by conventional methods for separation in a suitable step.

The compounds of the general formula (I) wherein R represents a hydrogen atom may be converted into salts by known methods. The salts are preferably non-toxic and water-soluble. Suitable salt are, for example, a salt of such an alkali metal as sodium or potassium, a salt of such an alkaline earth metal as calcium or magnesium, or an ammonium salt or a non-toxic amine salt, for example, such a tetraalkylammonium salt as tetramethylammonium salt or such an organic amine salt as methylamine, dimethylamine, cyclopentylamine, benzylamine, phenetylamine, piperidine, monoethanolamine, diethanolamine, tris(hydroxymethyl)aminomethane, lysine or arginine salts.

EFFECT

The compounds of the general formula (I) and their non-toxic salts have a potent inhibitory effect on development of cerebral edema.

A group of diseases which cause cerebral edema is such diseases of cerebral ischemia as cerebral blood vascular damage (e.g. cerebral infarction, cerebral thrombosis), decrease of cerebral blood flow, cerebral ischemia, cerebral anoxia or spinal cord damage. In these diseases, because of the deficiency in oxygen supplied to organs, the level of energy production decreases, and then it becomes impossible to maintain the exchange reaction of $Na^+ \rightarrow K^+$ across the cell membrances by ATPase (adenosinetriphosphatase), and further the intracellular concentration of Na+ and Cl−
increases. Accordingly, because extracellular water is
taken into the cell, cerebral edema is developed. Another group of diseases which cause cerebral edema is
such diseases that brings about the physical compression as cephalic trauma or cerebral tumor. In these
diseases, it has been also considered that a damage in
cellular function by physical compression leads to Na+
influx followed by water influx into the cells, and the
edema is developed.

The compounds of the general formula (I) and their
non-toxic salts inhibit the influx of Na+ and Cl−, and of
water into cells and therefore potently inhibit the formation of cerebral edema. According they are useful for
the prevention of and the treatment of cerebral edema
caused by any diseases as mentioned above.

The inhibitory effect on cerebral edema of the compounds of the present invention is confirmed by the
following screening test.

The inhibition test on cerebral edema using organ slice
of cat cerebral cortex

The test was carried out by the method described in
Journal of Medicinal Chemistry, vol. 25 (No. 5) 567
(1982).

That is, brain was isolated from a cat weighing 2–4
kg, slices of about 1 mm in thickness was prepared, the
white matter substance was removed, and the gray
matter substance (100–150 mg a test) was used for a
sample. The sample was added to the following incubation medium and incuvated for 50 minutes at 37° C.
After the incubation, the sample was immediately
weighed again to determine the swelling weight of the
sample.

incubation medium (osmotic pressure, 280–290
mOsm/1)

1. Hepes Buffer (pH 7.4) . . . 2.365 ml
   glucose 10 mM
   $CaCl_2$ 1.3 mM
   $MgSO_4$ 1.2 mM
   $KH_2PO_4$ 1.2 mM
   Hepes 20 mM
   NaCl 122 mM
   KCl 20 mM
   adjusted to pH 7.4 by NaOH
2. test compounds [dissolved in the presence of tris(-hydroxymethyl)aminomethane] or water . . . 0.01 ml
3. 0.2M $NaHCO_3$ (dissolved by Hepes Buffer, giving the final concentration of 10 mM in medium) or Hepes Buffer . . . 0.125 ml The test was carried out by using $NaHCO_3$ as a stimulating agent of swelling.

(A) A percentage of swelling when a slice sample was added to incubation medium comprising Hepes Buffer (1), water (2) and $NaHCO_3$ (3) (defined as maximum of swelling).

(B) A percentage of swelling when a slice sample was added to incubation medium comprising Hepes Buffer ((1)+(3)) and water (2) (defined as maximum inhibition of swelling).

(C) A percentage of swelling when a slice sample was added to incubation medium comprising Hepes Buffer (1), the test compounds in various concentrations (2) and $NaHCO_3$ (3).

Above-mentioned (A), (B) and (C) were determined.
Inhibition percentage of the test compounds was caliculated by the following equation:

$$\text{inhibition \%} = \frac{(A) - (C)}{(A) - (B)} \times 100$$

$IC_{50}$ value was determined by dose-response curve as a concentration in which inhibition percentage was 50.
The results are shown below.

TABLE

| | Inhibitory effect on cerebral edema | | |
|---|---|---|---|
| | Example No. of test compound | Inhibitory activity cerebral edema ($IC_{50}$, M) | Relative activity (Compound A = 1) |
| Compounds of the present invention | Ex. 2 | $2.5 \times 10^{-9}$ | 12.8 |
| | Ex. 2 (a) | $1.5 \times 10^{-9}$ | 21.3 |
| | Ex. 2 (b) | $5.9 \times 10^{-9}$ | 5.42 |
| | Ex. 2 (c) | $1.6 \times 10^{-9}$ | 20.0 |
| Control | Compound A* | $3.2 \times 10^{-8}$ | 1 |

*Compound A: (+)-4-[((2R)-2-cyclopentyl-2-methyl-6,7-dichloro-1-oxoindan-5-yl)oxy]butyric acid (a compound described in Example 8 of the specification of the European Patent Publication No. 47011.)

On the other hand, it was confirmed that the acute
toxicity of the compounds of the present invention was
very weak. For example, in the acute toxicity test, the
$LD_{50}$ value of the compound prepared in Example 2(a)
was more than 200 mg/kg and less than 400 mg/kg
when administered intravenously. Therefore, compounds of the present invention may be considered to be
sufficiently safe and suitable for medical use.

For the purpose of the prevention and the treatment
for cerebral edema, the compounds of the general formula (I) or non-toxic salts thereof may normally be
administered systemically or partially, usually by oral
or parenteral administration. The dose to be administered is determined depending upon age, body weight,
symptom, the desired therapeutic effect, the route of
administration, and the duration of the treatment etc. In
the human adult, the doses per person for one time are
generally between 1 mg and 1 g, by oral administration
up to several times per day, and between 100 μg and 100
mg, by parenteral administration (preferably by intravenous administration) up to several times per day.

As mentioned above, the doses to be used depend on
various conditions. Therefore, there are cases in which
doses lower than the ranges specified above and doses
greater than the ranges specified above, may be used.

Solid compositions according to the present invention for oral administration include compressed tablets,
dispersible powders and granules. In such solid compositions, one or more of the active compound(s) is, or are,
admixed with at least one inert diluent such as lactose,
mannitol, glucose, hydroxypropyl cellulose, microcrystalline cellulose, starch, polyvinyl-pyrrolidone or magnesium metasilicate aluminate. The compositions may
also comprise, as is normal practice, additional substances other than inert diluents e.g. lubricating agents
such as magnesium stearate, and, disintegrating agents
such as cellulose calcium gluconate. The tablets or pills
may, if desired, be made into gastric film-coated or
enteric film-coated tablets or pills, such as sugar-coated,
gelatin-coated, hydroxypropylcellulose-coated or hydroxypropylmethylcellulose phthalate-coated tablets or
pills; two or more layers may be used. The compositions
for oral administration also include capsules of absorbable material such as gelatin.

Liquid compositions for oral administration include
pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods which comprise one or more of the active compound(s).

Preparations for injection according to the present invention for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, Polysorbate 80 (registered Trade Mark). These compositions may also include adjuvants such as preserving, wetting, eulsifying and dispersing agents. They may be sterilized, for example, by filtration through a bacteria-retaining filter, by incorporation of sterilizing agents in the compositions or by irradiation. They may also be manufactured in the form of sterile solid compositions which can be dissolved in sterile water dor some other sterile injectable medium immediately before use.

Other compositions for parenteral administration include liquids for external use, and endermic liniments such as ointments, suppositories for rectal administration and pessaries for vaginal administration which comprise one or more of the active (compound)s and may be prepared by known methods.

REFERENCE EXAMPLES AND EXAMPLES

The following Reference Examples and Examples illustrate the preparation of compounds of the present invention, however, the present invention is not restricted to them. In the Reference Examples and Examples, "TLC", "NMR", "IR" and "MS" represent "Thin layer chromatography", "Nuclear magnetic resonance spectrum", "Infrared absorption spectrum" and "Mass spectrum", respectively. The solvents in parenthesis specified in chromatographic separations show the developing solvents. Except when specified otherwise, infrared absorption spectra were recorded by the liquid film method and nuclear magnetic resonance spectra were recorded in deuterochloroform (CDCl$_3$) solution. In the structural formulae, "Ts" represents "p-toluenesulfonyl group (tosyl group)".

REFERENCE EXAMPLE 1

(2RS)-2-cyclopentyl-2-methyl-5-mercapto-6,7-dichloroindan-1-one

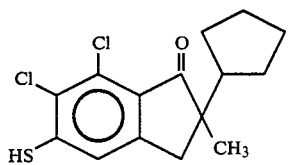

(1) (2RS)-2-cyclopentyl-2-methyl-5-trifluoromethanesulfonyloxy-6,7-dichloroindan-1-one To a solution of 600 mg of (2RS)-2-cyclopentyl-2-methyl-5-hydroxy-6,7-dichloroindan-1-one (prepared by the method described in European Patent Publication No. 47011) in 6 ml of dry acetone was added 690 mg of potassium carbonate at a time and the mixture was stirred for twenty minutes. The reaction mixture was cooled to 0° C., 0.23 ml of trifluoromethanesulfonyl chloride was dropped thereto and the mixture was stirred for 10 minutes at the same temperature. The solid was filtered out from the reaction mixture and the filtrate was concentrated under reduced pressure. The obtained residue was dissolved in methylene chloride and the solution was dried over anhydrous magnesium sulfate and concentrated under reduced pressure to give 860 mg of the title compound as crude product having the following physical data.

TLC (n-hexane:ethyl acetate=4:1): Rf 0.76

(2) (2RS)-2-cyclopentyl-2-methyl-5-acetylthio-6,7-dichloroindan-1-one

To a solution of 860 mg of 5-trifluoromethanesulfonyloxy compound prepared in (1) in 5 ml of dry dimethylformamide were added successively 0.288 ml of thioacetic acid CH$_3$COSH and 0.386 ml of diisopropylethylamine under cooled with ice, and the mixture was stirred for 1.5 hour at ambient. The reaction mixture was poured into 10 ml of the mixture of ice-1N hydrochloric acid (1:1), and the obtained mixture was extracted with diethyl ether. The extract was washed successively with water and a saturated aqueous solution of sodium chloride, and dried over anhydrous magnesium sulfate and then concentrated under reduced pressure. The residue was purified by column chromatography on silica gel (eluent, n-hexane:ethyl acetate=8:1) to give 300 mg of the title compound having the following physical data.

TLC (n-hexane:ethyl acetate=4:1): Rf 0.53;

IR: $\nu$1700, 1560, 1435, 1360, 1290, 1230, 1130, 1100, 1030, 990, 930, 830 cm$^{-1}$;

MS: m/z 314, 288, 246.

(3) (2RS)-2-cyclopentyl-2-methyl-5-mercapto-6,7-dichloroindan-1-one

To a solution of 300 mg of 5-acetylthio compound prepared in (2) in the mixture of 1.3 ml of methanol and 0.6 ml of tetrahydrofuran was dropped 1.35 ml of 5% aqueous solution of sodium hydroxide and the mixture was stirred for 20 minutes at ambient and then concentrated under reduced pressure. 2 ml of water was added to the residue and the mixture was acidified to pH 1 with 1N hydrochloric acid under cooled with ice. The mixture was extracted with diethyl ether and the extract was washed successively with water and a saturated aqueous solution of sodium chloride and dried over anhydrous magnesium sulfate and then concentrated under reduced pressure to give 210 mg of the title compound as crude product having following physical data.

TLC (n-hexane:ethyl acetate=4:1): Rf 0.21.

REFERENCE EXAMPLE 2

(±)-cis-3-tosyloxycyclopentanecarboxylic acid methyl ester

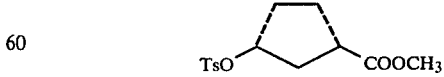

(1) 3-hydroxycyclopentanecarboxylic acid methyl ester

To a solution of 2.8 g of 3-oxocyclopentanecarboxylic acid in 20 ml of diethyl ether was added ethereal solution of diazomethane under cooled with ice until the mixture turned pale yellow, and then the reaction mixture was concentrated under reduced pressure to give about 3.1 g of 3-oxocyclopentanecarboxylic acid methyl ester as crude product. Obtained methyl ester compound was dissolved in 20 ml of methanol and after the mixture was cooled to −50° C., 820 mg of sodium borohydride was added thereto at a time and the mixture was stirred for 20 minutes at the same temperature. After 1.3 ml of acetic acid was dropped slowly to the reaction mixture, methanol was removed under reduced pressure. To the residue was added 10 ml of water and the mixture was extracted with ethyl acetate and the extract was washed successively with water and a saturated aqueous solution of sodium chloride and dried over anhydrous magnesium sulfate and concentrated under reduced pressure to give 3 g of the title compound as crude product having the following physical data.

TLC (n-hexane:ethyl acetate=1:2): Rf 0.51;
IR: $\nu$3400, 1720, 1430, 1360, 1190, 1020 cm$^{-1}$.

(2) (±)-cis-3-tosyloxycyclopentanecarboxylic acid methyl ester

To a solution of 3 g of 3-hydroxy compound prepared in (1) in 19 ml of pyridine was added 6.7 g of tosyl chloride and the mixture was stirred for 5 hours at ambient. The reaction mixture was diluted with ethyl acetate and the mixture was washed successively with water, a saturated aqueous solution of cupric sulfate and water, and dried over anhydrous magnesium sulfate and concentrated under reduced pressure. The residue was purified by column chromatography on silica gel (eluent, n-hexane:ethyl acetate=2:1) to give 3.4 g of the title compound having the following physical data and 0.8 g of the corresponding trans isomer.

(i) cis isomer

TLC (n-hexane:ethyl acetate=1:1): Rf 0.48;
NMR: $\delta$7.78(2H, d), 7.32(2H, d), 4.93(1H, m), 3.66(3H, s), 2.72(1H, q), 2.44(3H, s);
IR: $\nu$1720, 1590, 1430, 1350, 1170, 1090, 880, 650 cm$^{-1}$.

(ii) trans isomer

TLC (n-hexane:ethyl acetate=1:1): Rf 0.57.

REFERENCE EXAMPLE 3

(1S, 3R)-3-tosyloxycyclopentanecarboxylic acid methyl ester

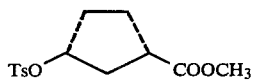

By the same procedure as described in Reference Example 2 (1) and (2), the title compound having the following physical data was obtained.

Starting material: (1S)-3-oxocyclopentanecarboxylic acid;
Optical rotation: $[\alpha]_D^{25}$ +15.2° (c=0.5, ethanol);
TLC (n-hexane:ethyl acetate=1:1): Rf 0.48;
NMR: $\delta$7.78(2H, d), 7.32(2H, d), 4.93(1H, m), 3.66(3H, s), 2.72(1H, q), 2.44(3H, s);
IR: $\nu$1720, 1590, 1430, 1350, 1170, 1090, 880, 650 cm$^{-1}$.

EXAMPLE 1

1,3-trans-3-[((2RS)-2-cyclopentyl-2-methyl-6,7-dichloro-1-oxoindan-5-yl)oxy]cyclopentanecarboxylic acid methyl ester

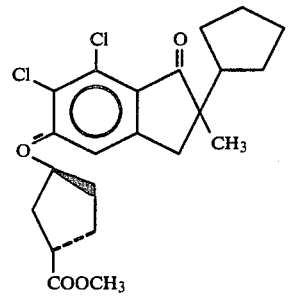

To a solution of 100 mg of (2RS)-2-cyclopentyl-2-methyl-5-hydroxy-6,7-dichloroindan-1-one (prepared by the method described in European Patent Publication No. 47011) in 1 ml of dry tetrahydrofuran was added 14.1 mg of sodium hydride (content: 62.7%) at a time at ambient and the mixture was stirred for 10 minutes at the same temperature. To the obtained reaction mixture was dropped a solution of 200 mg of tosylate compound (cis isomer prepared in Reference Example 2) in 1 ml of hexamethylphosphoramide at ambient and the mixture was stirred for 3 hours at 50° C. To the reaction mixture was added 0.5 ml of a saturated aqueous solution of ammonium chloride and after the mixture was diluted with 5 ml of water, the solution was extracted with diethyl ether. The extract was washed successively with water and a saturated aqueous solution of sodium chloride and dried over anhydrous magnesium sulfate and concentrated under reduced pressure. The residue was purified by column chromatography on silica gel (eluent, n-hexane:ethyl acetate=4:1) to give 95 mg of the title compound having the following physical data.

TLC (n-hexane:ethyl acetate=4:1): Rf 0.29;
IR: $\nu$1720, 1700, 1570, 1430, 1400, 1360, 1290, 1260, 1150, 1040 cm$^{-1}$.

By the same procedure as described in Example 1, the following compounds were obtained.

(a) (1S, 3S)-3-[((2RS)-2-cyclopentyl-2-methyl-6,7-dichloro-1-oxoindan-5-yl)oxy]cyclopentanecarboxylic acid methyl ester

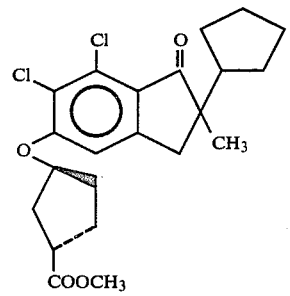

Starting materials: (2RS)-2-cyclopentyl-2-methyl-5-hydroxy-6,7-dichloroindan-1-one (prepared by the method described in European Patent Publication No.

47011) and tosylate compound prepared in Reference Example 3;

TLC (n-hexane:ethyl acetate=4:1): Rf 0.29;

IR: ν1720, 1700, 1570, 1430, 1400, 1360, 1290, 1260, 1150, 1040 cm$^{-1}$.

(b) (1S, 3S)-3-[((2RS)-2-cyclopentyl-2-methyl-6,7-dichloro-1-oxoindan-5-yl)thio]cyclopentanecarboxylic acid methyl ester

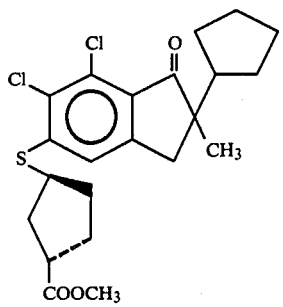

Starting materials: 5-mercapto compound prepared in Reference Example 1 and tosylate compound prepared in Reference Example 3;

TLC (n-hexane:ethyl acetate=4:1): Rf 0.40;

NMR: δ7.14(1H, s), 3.84(1H, q), 3.70(3H, s), 3.08(1H, q), 2.99(1H, d), 2.68(1H, d), 1.58(3H, s), 1.22(3H, s).

IR: ν1695, 1550, 1420, 1370, 1290, 1190, 1130, 990, 830 cm$^{-1}$;

MS: m/z 440(M+), 409, 372.

(c) (1S, 3S)-3-[((2S)-2-cyclopentyl-2-methyl-6,7-dichloro-1-oxoindan-5-yl)oxy]cyclopentanecarboxylic acid methyl ester

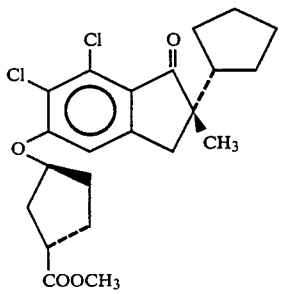

Starting materials: (2S)-2-cyclopentyl-2-methyl-5-hydroxy-6,7-dichloroindan-1-one (prepared by the method described in Journal of Medicinal Chemistry, vol. 18, 225 (1975)) and tosylate compound prepared in Reference Example 3;

TLC (n-hexane:ethyl acetate=4:1): Rf 0.42;

NMR: δ6.81(1H, s), 5.00(1H, m), 3.71(3H, s), 3.15(1H, m), 2.97(1H, dd), 2.66(1H, dd), 1.23(3H, s);

IR: ν1700, 1570, 1430, 1290, 1260, 1140, 1040, 750 cm$^{-1}$.

EXAMPLE 2

1,3-trans-3-[((2RS)-2-cyclopentyl-2-methyl-6,7-dichloro-1-oxoindan-5-yl)oxy]cyclopentanecarboxylic acid

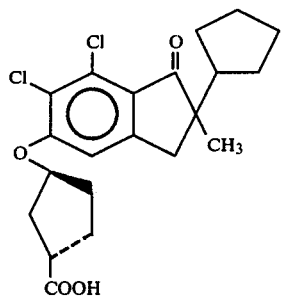

To a solution of 90 mg of methyl ester compound (prepared in Example 1) in the mixture of 0.7 ml of ethanol and 0.7 ml of tetrahydrofuran was dropped 0.64 ml of 5% aqueous solution of sodium hydroxide under cooled with ice and after the mixture was stirred for 1 hours at ambient, it was concentrated under reduced pressure. To the residue was added 2 ml of water and the mixture was acidified to pH 1 with 1N hydrochloric acid under cooled with ice. The mixture was extracted with ethyl acetate, and the extract was washed successively with water and a saturated aqueous solution of sodium chloride and dried over anhydrous magnesium sulfate and concentrated under reduced pressure to give 80 mg of the title compound having the following physical data.

TLC (n-hexane:ethyl acetate=1:4): Rf 0.50;

NMR: δ6.80(1H, s), 5.00(1H, bs), 3.20(1H, m), 2.98(1H, d), 2.66(1H, d), 1.22(3H, s);

IR (KBr method): ν3450, 1695, 1570, 1430, 1400, 1290, 1130, 1040 cm$^{-1}$;

MS: m/z 410(M+), 340.

By the same procedure as described in Example 2, the following compounds were obtained.

(a) (1S, 3S)-3-[((2RS)-2-cyclopentyl-2-methyl-6,7-dichloro-1-oxoindan-5-yl)oxy]cyclopentanecarboxylic acid

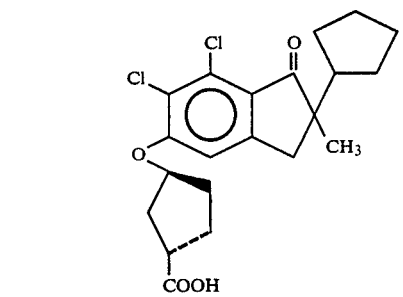

Starting material: methyl ester compound prepared in Example 1 (a);

TLC (n-hexane:ethyl acetate=1:4): Rf 0.50;

NMR: δ6.80(1H, s), 5.01(1H, bs), 3.21(1H, m), 2.98(1H, d), 2.66(1H, d), 1.22(3H, s);

IR (KBr method): ν3450, 1695, 1570, 1440, 1400, 1290, 1140, 1040 cm$^{-1}$;

MS: m/z 342.

(b) (1S, 3S)-3-[((2RS)-2-cyclopentyl-2-methyl-6,7-dichloro-1-oxoindan-5-yl)thio]cyclopentanecarboxylic acid

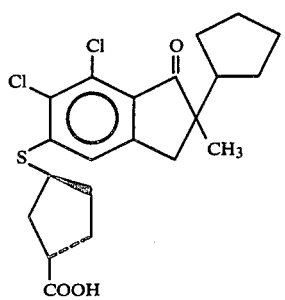

Starting materials: methyl ester compound prepared in Example 1 (b);

TLC (n-hexane:ethyl acetate=1:2): Rf 0.44;

NMR: δ7.14(1H, s), 3.86(1H, m), 3.13(1H, q), 2.98(1H, d), 2.68(1H, d), 1.22(3H, s);

IR (KBr method): ν3400, 1700, 1560, 1430, 1370, 1300, 1230, 1130, 990, 830 cm$^{-1}$;

MS: m/z 426(M$^+$), 358.

(c) (1S, 3S)-3-[((2S)-2-cyclopentyl-2-methyl-6,7-dichloro-1-oxoindan-5-yl)oxy]cyclopentanecarboxylic acid

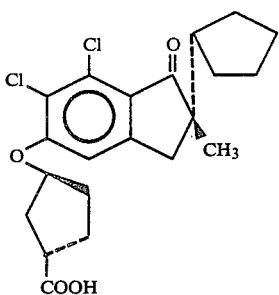

Starting materials: methyl ester compound prepared in Example 1 (c);

Optical rotation: [α]$_D^{25}$ −11.6° (c=0.5, methanol);

TLC: (ethyl acetate): Rf 0.53;

NMR: δ6.80(1H, s), 5.01(1H, m), 3.20(1H, m) 2.98(1H, d), 2.66(1H, d), 1.23(3H, s);

IR (KBr method): ν3400(br), 1695, 1570, 1430, 1290, 1130, 1040 cm$^{-1}$.

EXAMPLE 3

500 mg of (1S, 3S)-3-[((2RS)-2-cyclopentyl-2-methyl-6,7-dichloro-1-oxoindan-5-yl)oxy]cyclopentanecarboxylic acid prepared in Example 2 (a) was dissolved in 5 ml of ethanol and the solution was sterilized by filtration through a bacteria-retaining filter, and placed in 0.1 ml portions in 1 ml ampoules to obtain ampoules each containing 10 mg of the active ingredient, and the ampoules were then sealed. The contents of ampoules are used for injection by diluting with a suitable quantity of dilution, for example, by diluting with a tris-hydrochloric acid buffer solution (pH 8.6) to 1 ml.

We claim:

1. A 3-(indan-5-yloxy (or thio))cyclopentanecarboxylic acid analogue of the general formula:

(I)

wherein X represents an oxygen atom or a sulfur atom and R represents a hydrogen atom or an alkyl group of 1–4 carbon atoms; or a non-toxic salt thereof when R represents a hydrogen atom.

2. An analogue according to claim 1, wherein X represents an oxygen atom.

3. An analogue according to claim 1, wherein X represents a sulfur atom.

4. An analogue according to claim 1, wherein R represents an alkyl group of 1–4 carbon atoms.

5. An analogue according to claim 1, wherein R represents a hydrogen atom.

6. An analogue according to claim 1, which is 1,3-trans-3-[((2RS)-2-cyclopentyl-2-methyl-6,7-dichloro-1-oxoindan-5-yl)oxy]cyclopentanecarboxylic acid or its methyl ester, (1S, 3S)-3-[((2RS)-2-cyclopentyl-2-methyl-6,7-dichloro-1-oxoindan-5-yl)oxy]cyclopentanecarboxylic acid or its methyl ester, (1S, 3S)-3-[((2RS)-2-cyclopentyl-2-methyl-6,7-dichloro-1-oxoindan-5-yl)thio]cyclopentanecarboxylic acid or its methyl ester, or (1S, 3S)-3-[((2S)-2-cyclopentyl-2-methyl-6,7-dichloro-1-oxoindan-5-yl)oxy]cyclopentanecarboxylic acid or its methyl ester.

7. A composition for treating cerebral edema which comprises an effective amount of a 3-(indan-5-yloxy (or thio)cyclopentanecarboxylic acid analogue of the general formula:

(I)

wherein X represents an oxygen atom or a sulfur atom and R represents a hydrogen atom or an alkyl group of 1–4 carbon atoms; or a non-toxic salt thereof when R represents a hydrogen atom and a pharmaceutically acceptable carrier.

* * * * *